United States Patent
Parker et al.

(10) Patent No.: US 10,245,082 B2
(45) Date of Patent: *Apr. 2, 2019

(54) MINIMALLY INVASIVE SPLITABLE PEDICLE SCREW EXTENDER

(71) Applicant: Zimmer Biomet Spine, Inc., Broomfield, CO (US)

(72) Inventors: Jared Parker, Denver, CO (US); Michael Funk, Broomfield, CO (US); Randall G. Mast, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 215 days.

This patent is subject to a terminal disclaimer.

(21) Appl. No.: 15/160,373

(22) Filed: May 20, 2016

(65) Prior Publication Data

US 2016/0338744 A1 Nov. 24, 2016

Related U.S. Application Data

(63) Continuation of application No. 13/841,405, filed on Mar. 15, 2013, now Pat. No. 9,370,383.

(51) Int. Cl.
*A61B 17/70* (2006.01)

(52) U.S. Cl.
CPC ...... *A61B 17/7083* (2013.01); *A61B 17/7037* (2013.01); *A61B 17/7038* (2013.01); *A61B 17/7074* (2013.01); *A61B 17/7076* (2013.01)

(58) Field of Classification Search
CPC . A61B 17/70; A61B 17/7037; A61B 17/7038; A61B 17/7074–17/708
See application file for complete search history.

(56) References Cited

U.S. PATENT DOCUMENTS

| | | | |
|---|---|---|---|
| 8,211,110 B1 | 7/2012 | Corin et al. | |
| 8,439,922 B1 | 5/2013 | Arnold et al. | |
| 8,603,094 B2 | 12/2013 | Walker et al. | |
| 9,192,415 B1 | 11/2015 | Arnold et al. | |
| 9,211,149 B2 | 12/2015 | Hoefer et al. | |
| 9,220,543 B2 | 12/2015 | Walker et al. | |
| 9,370,383 B2 | 6/2016 | Parker et al. | |
| 9,492,209 B2* | 11/2016 | Biedermann | A61B 17/7085 |
| 9,629,661 B2* | 4/2017 | Kraus | A61B 17/708 |
| 9,980,758 B2* | 5/2018 | Abidin | A61B 17/7091 |

(Continued)

FOREIGN PATENT DOCUMENTS

WO PCT/US2014/028610 A1 9/2014

OTHER PUBLICATIONS

U.S. Appl. No. 13/841,405, filed Mar. 15, 2013, Minimally Invasive Splitable Pedicle Screw Extender.

(Continued)

*Primary Examiner* — Ellen C Hammond
*Assistant Examiner* — Tessa Matthews
(74) *Attorney, Agent, or Firm* — Schwegman Lundberg & Woessner, P.A.

(57) ABSTRACT

The present application provides a tool for minimally invasive surgical procedures. The tool includes a first and second portion where each portion has an outer blade and an inner blade that is slidable along the outer blade. A removable connector connects the first and second portions. When removed, the first and second portions are separated by a gap extending the length of the tool.

19 Claims, 8 Drawing Sheets

(56) References Cited

U.S. PATENT DOCUMENTS

| | | |
|---|---|---|
| 2002/0116006 A1 | 8/2002 | Cohen |
| 2005/0131408 A1 | 6/2005 | Sicvol et al. |
| 2006/0074418 A1* | 4/2006 | Jackson ............ A61B 17/7086 606/914 |
| 2006/0079909 A1* | 4/2006 | Runco ............... A61B 17/7076 606/99 |
| 2007/0233079 A1 | 10/2007 | Fallin et al. |
| 2008/0077134 A1* | 3/2008 | Dziedzic ........... A61B 17/8875 606/86 A |
| 2009/0143828 A1* | 6/2009 | Stad .................. A61B 17/7085 606/86 A |
| 2009/0149892 A1 | 6/2009 | Stad et al. |
| 2011/0034962 A1 | 2/2011 | Dunbar, Jr. et al. |
| 2011/0313463 A1 | 12/2011 | Mclean |
| 2012/0022594 A1 | 1/2012 | Walker et al. |
| 2012/0035668 A1 | 2/2012 | Manninen et al. |
| 2012/0116460 A1 | 5/2012 | Gorek |
| 2013/0245702 A1* | 9/2013 | McBride ............ A61B 17/7076 606/305 |
| 2013/0245705 A1* | 9/2013 | McBride ............ A61B 17/7032 606/86 R |
| 2014/0039567 A1* | 2/2014 | Hoefer ................ A61B 17/708 606/86 A |
| 2014/0052187 A1* | 2/2014 | McBride ............. A61B 17/708 606/264 |
| 2014/0148865 A1* | 5/2014 | Hennard ........... A61B 17/7086 606/86 A |
| 2014/0277200 A1 | 9/2014 | Parker et al. |
| 2014/0316475 A1 | 10/2014 | Parikh et al. |
| 2015/0039035 A1 | 2/2015 | Krüger |
| 2015/0051648 A1 | 2/2015 | May et al. |
| 2015/0066042 A1* | 3/2015 | Cummins .......... A61B 17/7037 606/104 |
| 2015/0073485 A1 | 3/2015 | Butler |
| 2015/0359571 A1 | 12/2015 | Biedermann et al. |
| 2017/0079696 A1* | 3/2017 | Walker ................ A61B 17/708 |
| 2017/0164985 A1* | 6/2017 | Reitblat ............. A61B 17/7085 |
| 2018/0008318 A1* | 1/2018 | Fiechter ............... A61B 17/708 |

OTHER PUBLICATIONS

"European Application Serial No. 14763415.8, Extended European Search Report dated Nov. 7, 2016", 7 pgs.

"European Application Serial No. 14763415.8, Response filed Jun. 6, 2017 to Extended European Search Report dated Nov. 7, 2016", 8 pgs.

"U.S. Appl. No. 13/841,405, Advisory Action dated Jan. 21, 2016", 5 pgs.

"U.S. Appl. No. 13/841,405, Final Office Action dated Oct. 1, 2015", 19 pgs.

"U.S. Appl. No. 13/841,405, Non Final Office Action dated Apr. 23, 2015", 15 pgs.

"U.S. Appl. No. 13/841,405, Notice of Allowance dated Feb. 22, 2016", 9 pgs.

"U.S. Appl. No. 13/841,405, Response filed Jul. 23, 2015 to Non Final Office Action dated Apr. 23, 2015", 12 pgs.

"U.S. Appl. No. 13/841,405, Response filed Oct. 17, 2014 to Restriction Requirement dated Sep. 11, 2014", 7 pgs.

"U.S. Appl. No. 13/841,405, Response filed Dec. 28, 2015 to Final Office Action dated Oct. 1, 2015", 14 pgs.

"U.S. Appl. No. 13/841,405, Restriction Requirement dated Sep. 11, 2014", 7 pgs.

"U.S. Appl. No. 13/841,405, Resubmitted Response Filed Feb. 3, 2016 to Final Office Action dated Oct. 1, 2015", 14 pgs.

"International Application Serial No. PCT/US2014/028610, International Preliminary Report on Patentability dated Sep. 24, 2015", 10 pgs.

"International Application Serial No. PCT/US2014/028610, International Search Report dated Jul. 24, 2014", 4 pgs.

"International Application Serial No. PCT/US2014/028610, Written Opinion dated Jul. 24, 2014", 8 pgs.

\* cited by examiner

MINIMALLY INVASIVE SPLITABLE PEDICLE SCREW EXTENDER

REFERENCE TO RELATED PATENT APPLICATIONS

The present application for patent is related to U.S. patent application Ser. No. 13/540,497, titled MINIMALLY INVASIVE TOOL TO FACILITATE IMPLANTING A PEDICEL SCREW AND HOUSING, which is a continuation of U.S. patent application Ser. No. 11/938,073, titled MINIMALLY INVASIVE TOOL TO FACILITATE IMPLANTING A PEDICLE SCREW AND HOUSING, filed Nov. 9, 2007, now issued as U.S. Pat. No. 8,211,110, which claims priority to United States Provisional Patent Application Ser. No. 60/865,365, filed Nov. 10, 2006, all of which are herein incorporated by reference as if set out in full.

BACKGROUND

Background

Spinal fusion is a known technique to correct spinal injuries, deformities, and/or degenerative conditions. Lumbar fusion, for example, is generally an open procedure. An open procedure includes making a relatively large surgical incision to access the surgical site. A surgeon may implant a fusion cage into an intervertebral disc space, Next, the surgeon immobilizes the adjacent vertebral bodies using fixation rods attached to the superior and inferior vertebral body. Immobilizing the superior and inferior vertebral body allows hone to grow and fuse the superior and inferior bodies into one mass of bone.

As can be appreciated, the open procedure described above results in a relatively significant amount of trauma to the patient as a significant amount of tissue and muscle must be cut and retracted to allow access to the surgical site. Minimally invasive tools and procedures have been developed to reduce the amount of trauma as well as reduce the recovery time. One such minimally invasive system includes the '110 Patent disclosed above. The '110 Patent allows for a smaller or minimal incision by providing a surgical corridor formed by inner and outer sleeves that locked to a pedicle screw or a pedicle screw tulip. A surgeon accesses the surgical site through the surgical corridor formed by the sleeves.

Another minimally invasive tool is disclosed by U.S. Pat. No. 7,951,175, titled INSTRUMENTS AND METHODS FOR MANIPULATING A VERTEBRA, issued May 31, 2011, and incorporated herein by reference as if set out in full. The '175 Patent similarly describes a tool that forms a corridor and connects to a bone anchor. The '175 Patent has a proximal end extending from the patient. The inner sleeve of the instrument is movable relatively to the outer sleeve, via a plunger or the like, that resides along the center line of the corridor formed by the tool. The instrument 10 disclosed by the '175 Patent provides for a minimally invasive mechanism to manipulate the vertebrae and to seat the rods 90A, 90B into the bone anchors, but does not provide a convenient mechanism to move the rods 90A, 90B from outside the patient to inside the patient.

Other similarly minimally invasive tools provide a special rod introduction tool. For example, United States Published Patent Application Publication Number 2012/0253402A1, filed Jun. 14, 2012, titled PEDICLE SCREW EXTENSION FOR USE IN PERCUTANEOUS SPINAL FUSION, the disclosure of which is incorporated herein as if set out in full, provides for a rod introducer that slidingly engages the outside of a pedicle screw extension and moves a rod into position as the tool slides from a proximal to a distal location along the extension. The tool of the '340 application, as well as other similar pedicle screw extenders as they are generally know in the art, leaves much to be desired. In particular, rod introducers for the current extenders are customer tools that are adapted to engage the outside of the extender, rather than using the hollow center of the extenders. The rod introducer is offset from the pedicle screw extender requiring a slightly larger incision. Also, the pedicle screw extenders themselves, as presently constructed, provide an obstructed view of the surgical area.

Thus, against the above background, an improved pedicle screw extender would be desirable.

BRIEF DESCRIPTION OF THE DRAWINGS

Various examples of the technology of the present application will be discussed with reference to the appended drawings. These drawings depict only illustrative examples of the technology described more fully herein and are not to be considered limiting of its scope.

DETAILED DESCRIPTION

The technology of the present application will be described in the context of spinal surgery, but one of ordinary skill in the art will recognize on reading the disclosure that the technology may be applicable to other medical fields. Moreover, the technology of the present application will be described with reference to certain exemplary embodiments. The word "exemplary" is used herein to mean "serving as an example, instance, or illustration." Any embodiment described herein whether or not specifically identified as "exemplary" is not to be construed as preferred or advantageous over other embodiments. Moreover, in certain instances only a single "exemplary" embodiment is provided. A single example is not necessarily to be construed as the only embodiment. It also should be understood that terminology employed herein is used for the purpose of describing particular embodiments only and is not intended to be limiting. It must be rioted that, as used in this specification, the singular forms "a," "an," and "the" include plural references unless the context of the disclosure clearly dictates otherwise. Thus, for example, reference to "a lithium hydroxide" is not to be taken as quantitatively or source limiting, reference to "a step" may include multiple steps, reference to "producing" or "products" of a reaction should not be taken to be all of the products of a reaction, and reference to "reacting" may include reference to one or more of such reaction steps. As such, the step of reacting can include multiple or repeated reaction of similar materials to produce identified reaction product.

Further, the instrument(s) described in accordance with the technology of the present application facilitate surgical implantation of pedicles screws and fixation rods for spinal fusion. With that in mind, exemplary spinal fixation systems may include polyaxial or monoaxial pedicle screws as are generally understood in the art. Moreover, the instruments may be useful for surgery relating to fixation of the cervical, thoracic, and/or lumbar spine. Additionally, the instruments may be useful in other orthopedic fusion procedures where two or more boney segments are to be fused using rods and screws to immobilize the segments.

The detailed description includes specific details for the purpose of providing a thorough understanding of the technology of the present patent application. However, on reading the disclosure, it will be apparent to those skilled in the art that the technology of the present patent application may be practiced with or without these specific details. In some descriptions herein, generally understood structures and devices may be shown in block diagrams to aid in understanding the technology of the present patent application without obscuring the technology herein.

Figure 1:
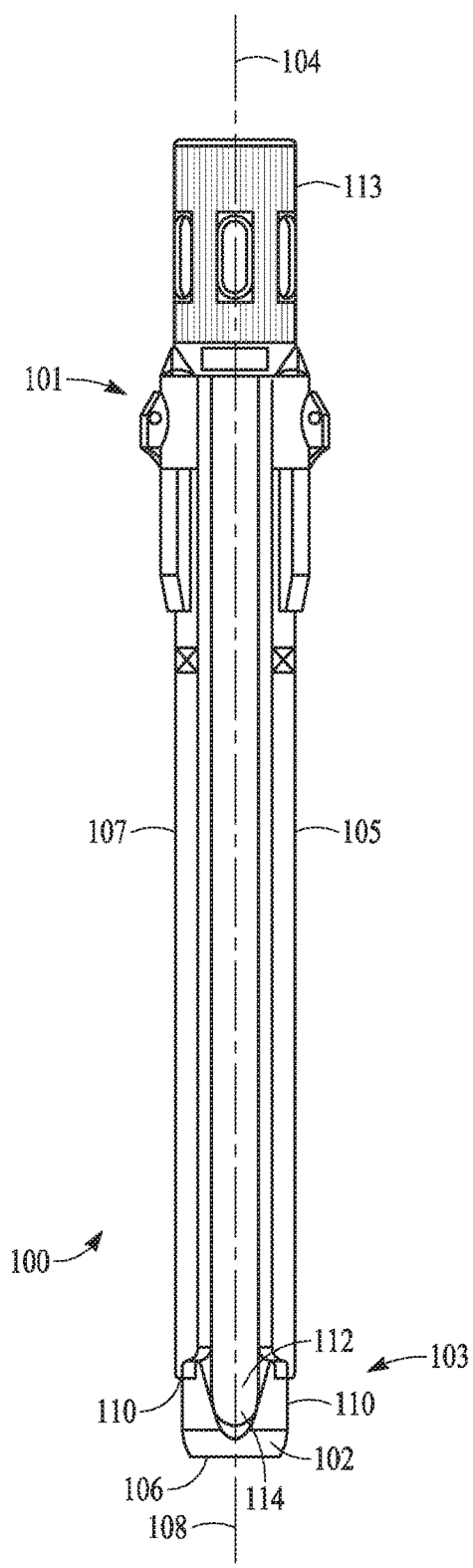
FIG. 1 is a view of a toot connected to a saddle consistent with the technology of the present application.
Figure 2:
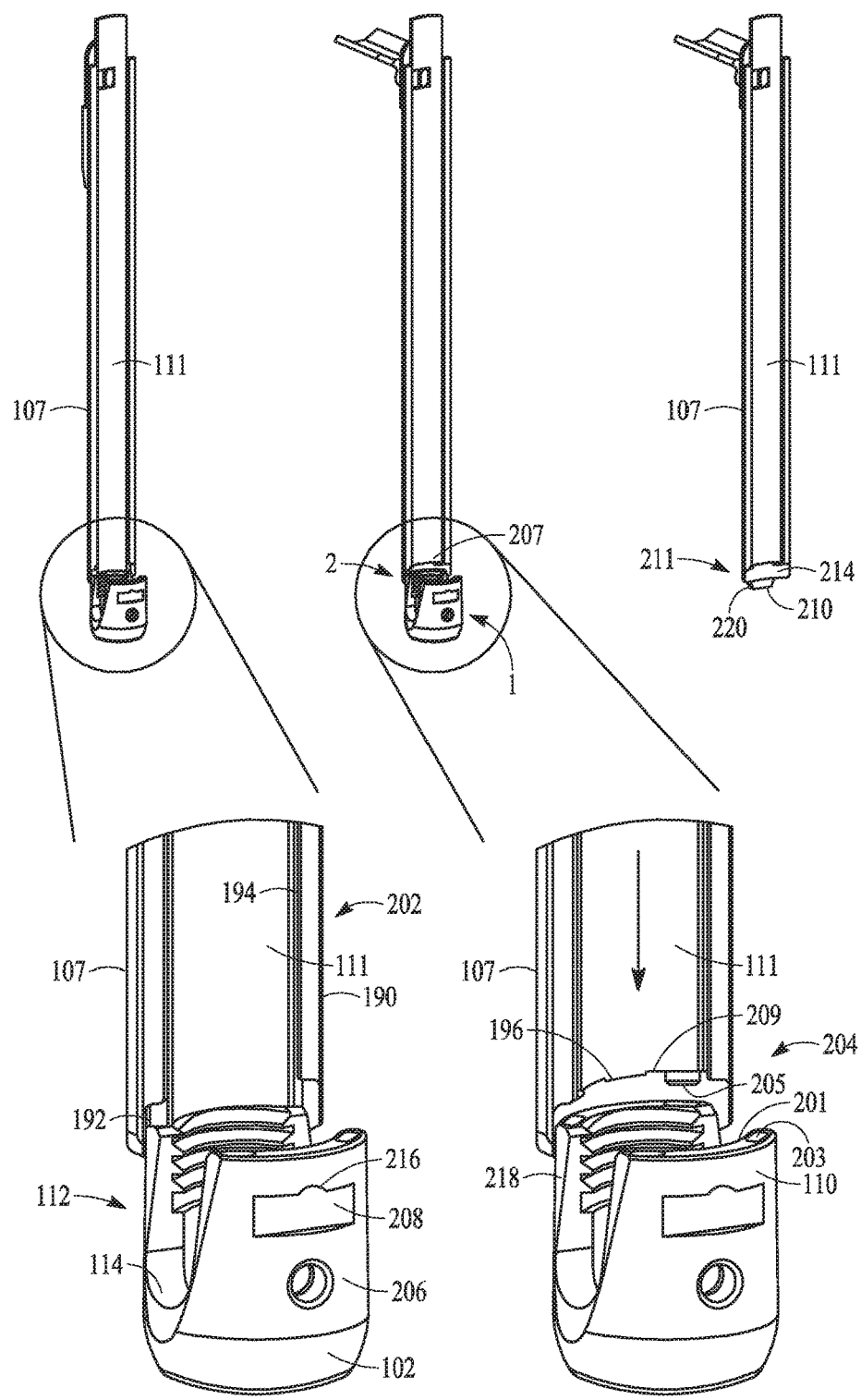
FIG. 2 is another view of the tool connected to the saddle as shown in FIG. 1.

Referring first to FIGS. 1 and 2, a tool 100 coupled to a saddle 102 is provided. The saddle 102 is a portion of an implant usable in pedicle screw and rod fixation systems as is generally known in the art. It should be noted that saddle 102 may be a number of different implants, however. The tool 100 has a proximal end 101 and a distal end 103. The tool 100 has a longitudinal axis 104 extending between first and second outer blades or elongate members 105, 107. With reference to FIG. 2, the tool 100 also has first and second inner blades or elongate members 109, 111. The blades 105, 107, 109, 111 as shown may have an arc or radius to facilitate a sliding interconnect between the first inner and first outer blades 105, 109 and the second inner and second outer blades 107, 111. The blades 105, 107, 109, 111, cooperate to releasably couple to the saddle 102 at the distal end 103, as will be explained further below. The outer surfaces of the first and second inner blades 109, 111 slidingly engage the inner surfaces of the first and second outer blades 105, 107 such that the first and second inner blades 109, 111 have an unlocked position 204 where the tool 100 is releasably engageable with the saddle 102 and a locked position 202 where the tool 100 is locked to the saddle 102.

The proximal end 101 further comprises a connector 113 that releasably couples the blades 105, 107, 109, 111 at the proximal end 101 of the tool, as also will be explained further below. The connector 113 is adapted to couple the blades 105, 107, 109, 111 at the proximal end 101 but does not cause relative movement of the first and second inner blades 101, 111 with respect to the first and second outer blades 105, 107. When connector 113 is coupled to the tool 100, the first and second inner blades 109, 111, and the first and second outer blades 105, 107 may be considered inner and outer sleeves, tubes, lumen, or the like. When the connector 113 is removed, however, the blades are not otherwise interconnected unless an external C-clip or the like is provided for rigidity. Removing the interconnection provides a channel, defined below, over the entire length of the tool 100.

With continued reference to FIGS. 1 and 2, one possible saddle 102 will be further described. The saddle 102 comprises a through bore 106 with a bore axis 108 generally aligned with the vertical longitudinal axis 104. The saddle 102 also comprises a plurality of legs 110 (or arms) forming a U-shaped channel 112 having a rod seat 114. The through bore 106 is configured to receive a bone fastener as is generally known in the art, but not shown for convenience. The U-shaped channel 112 and rod seat 114 are configured to receive a fixation rod as is generally known in the art, but not shown for convenience.

With reference to FIG. 2, an exemplary attachment mechanism 1 and 2 for establishing a releasable connection between the inner and outer blades of tool 100 and the saddle 102 will now be explained. Additional detail regarding the connection is provided in U.S. Pat. No. 8,211,110 incorporated by reference above. FIG. 2 shows the tool 100 and the saddle 102 in a locked position 202 and an unlocked position 204. As can be appreciated, the first and second outer blades 105, 107 may have a rolled or folded edge 190 forming a groove 192. The first and second inner blades 109, 111 may have a tongue 194 forming a slidable tongue and groove connection between the inner and outer blades.

The attachment mechanism 2 is further described with reference to the unlocked position 204. The legs 110 of the saddle terminate at an upper surface 201. The upper surface 201 has at least one locking detent 203 sized to receive a locking protrusion 205 extending from a distal end. 207 of the first and second inner blades 109, 111. In this exemplary embodiment, two locking protrusions 205 are provided to engage two locking detents 203. To facilitate the connections, the distal end of the first and second inner blades 109, 111 may include a wedge, block, ramp 196, or the like. The ramp 196 tends to bias the first and second inner blades radially outwardly.

The attachment mechanism 1 is further described with reference to the locked position 202. The legs 110 include an outer surface 206. The outer surface 206 has a tool shelf 208. The first and second outer blades 105, 107 have a ledge 210 extending radially inwardly from the distal end 212 of the first and second outer blades 105, 107. The ledge 210 is sized to engage the shelf 208. The ledge 210 and shelf 208 may comprise alignment ridges and grooves 214, 216 as shown.

When in the unlocked position 204, the first and second blades 105, 107 are movable radially outwardly from each other. The first and second blades 105, 107 are initially positioned such that the opposed ledges 210 move into the U-shaped channel 112. The first and second blades 105, 107 are rotated, either clockwise or counterclockwise, such that the legs 110 of the saddle 102 force the first and second blades 105, 107 radially apart. The U-shaped channel 112 may have edges 218 that are beveled, tapered, or chamfered to facilitate the movement. The ledge 210 may have cooperating edges 220, which may be referred to as leading or trailing edges. The tool 110 is rotated and moved vertically until the ledge 210 aligns with the shelf 208, at which point the first and second blades move radially inward to "snap fit" onto the saddle 102.

Coupling the ledge 210 and shelf 208 generally aligns the locking protrusions 205 with the locking detents 203. The first and second inner blades 109, 111 are slid along the inner surface of the first and second outer blades 105, 107 until the locking protrusions 205 engage with the locking detents 203. A clamping force is generated between the bottom surface 209 of the first and second inner blades 109, 111 abutting the upper surface 201 of the saddle 102 and the ledge 210 of the first and second outer blades 105, 107 engaging the shelf 208.

The first and second inner blades 109, 111 in the locked position provide torsional resistance inhibiting the ability to rotate the tool 100 off the saddle 102. The resistance is provided in part because the locking protrusions 205 engaging the locking detents 203 inhibits the first and second outer blades 105, 107 from moving radially outward from each other and the clamping force described above, which inhibits the locking protrusions from skipping out of the locking detents 203.

Figure 3:
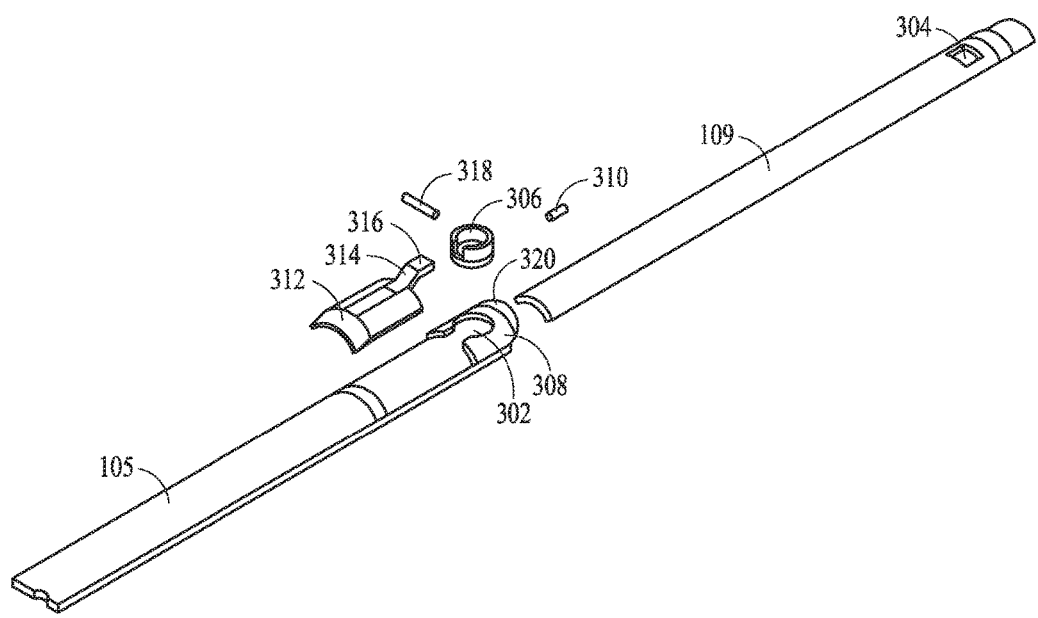
FIG. 3 is a partially exploded, perspective view of the tool of FIG. 1.

With reference now to FIG. 3, an exploded view of part of the tool 100 is shown. FIG. 3 shows the first outer blade 105 and the first inner blade 109. The second outer blade 107 and the second inner blade 111 would be substantially the same and are not further explained herein. The first outer blade 105 has an alignment bore 302 that generally aligns with an alignment window 304 of the first inner blade 109. The alignment bore 302 has a collar 308 extending outwardly from the first outer blade 105. The alignment bore 302 and the alignment window 304 align in an overlapping fashion, but generally move with respect to each other as will be explained further below.

Figure 4:
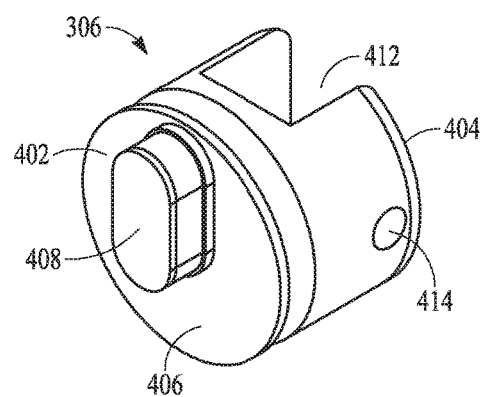
FIG. 4 is a perspective view of the turret of FIG. 3.
Figure 5:
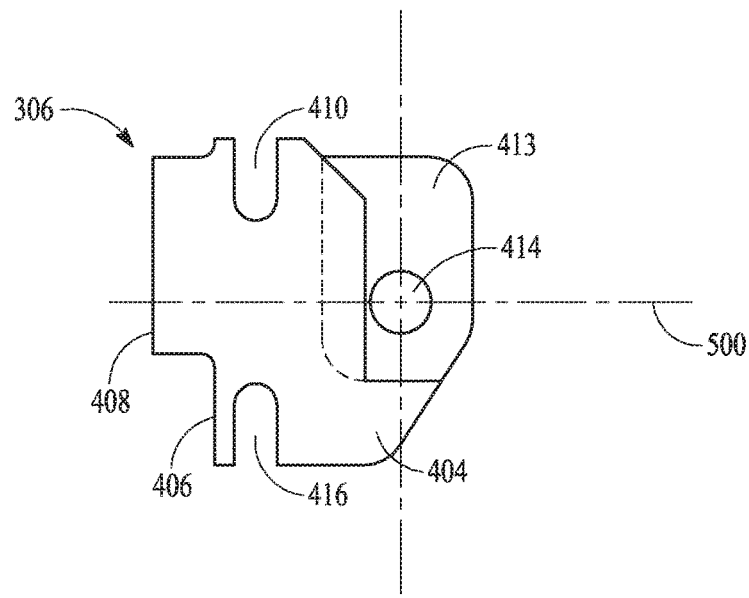
FIG. 5 is a cross sectional view of the turret of FIG. 4.

The alignment bore 302 is cylindrical and is sized to rotationally hold a turret 306, which is shown in more detail in FIGS. 4 and 5. The turret 306 includes an inside portion 402 and an outside portion 404. The inside portion 402 terminates in a face 406 that is generally aligned with the inside surface of the first and second outer blades 105, 107. Extending from the face 406 is a protrusion 408 or offset cam, which will be explained further below. The inside portion 402 is connected to the outside portion 404 by a beam 410 or web of material, which is shown in FIG. 5. The outside portion 404 includes a lever channel 412. The lever channel 412 is formed by walls 413 and is sized to receive an arm 314 of a lever 312. The arm 314 includes a rod bore 316 that aligns with the hinge bores 414. A rod 317 extends through the rod bore 316 and the hinge bores 414 to pivotally couple the lever 312 to the turret 306.

As can be appreciated, the alignment bore 302 and the turret 306 have generally the same diameter. The beam 410 coupling the inside portion 402 and the outside portion 404 has a reduced diameter and forms a cylindrical gap 416 between the inside portion 402 and the outside portion 404. An engagement pin 310 extends through an engagement bore 320 in the collar 308 and into the gap 416. The engagement pin 310 retains the turret 306 in the alignment bore 302 and allows for the turret 306 to rotate when the lever is moved in a clockwise or counterclockwise direction.

Figure 6:
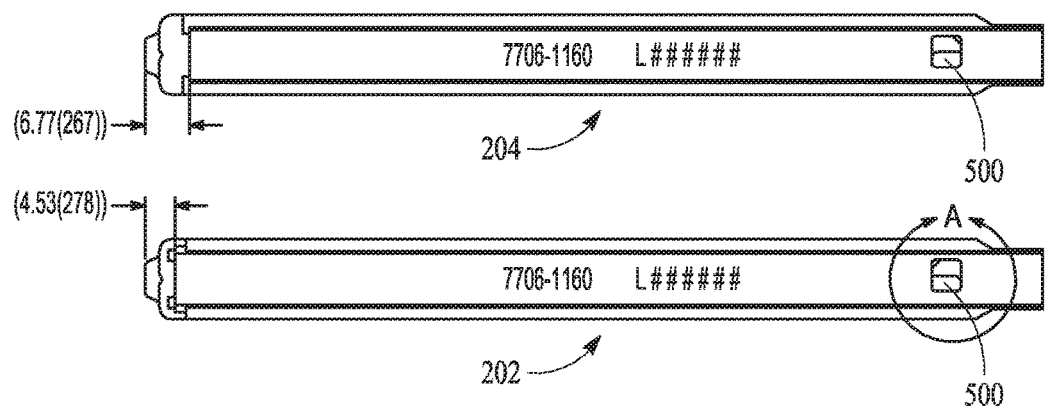
FIG. 6 is a view of movement of the turret and blades to move the tool from a locked to an unlocked position.

With reference to FIGS. 4 and 6, the turret 306 is shown with the tool 100 in the unlocked position 204 and the locked position 202. In the unlocked position 204, the protrusion 408 generally extends from the centerline 500 toward the proximal end 101 of tool 100 as shown in FIG. 4. In the locked position 202, the protrusion 408 generally extends from the centerline 500 toward the distal end 103 of tool 100. For reference, in the unlocked position 204, the protrusion 408 generally points to 12 o'clock and in the locked position 202, the protrusion generally points to 6 o'clock. The positions of turret 306 in the unlocked position 204 and the locked position 202 are shown in FIG. 6.

Figure 7:
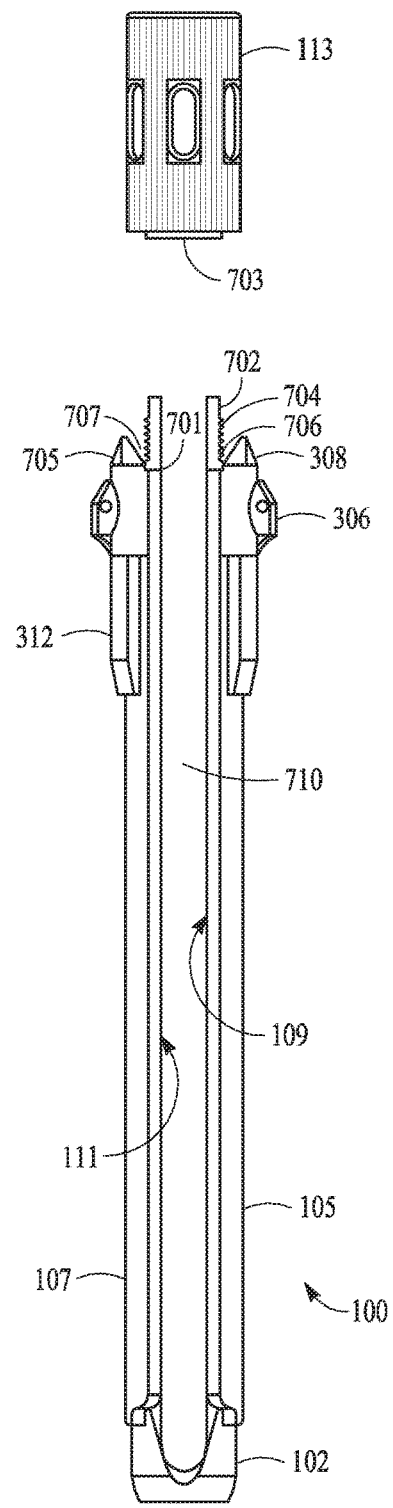
FIG. 7 is a partially exploded view of the tool of FIG. 1.

FIG. 7 shows a view of tool 100 with connector 113 exploded. Connector 113, in this exemplary embodiment, is a threaded connector. An alternative connector is described below. The outer surface of the first and second inner blades includes a top non-threaded panel 702 with a threaded panel 704 just below the top non-threaded panel 702 having a plurality of threads 706. The top non-threaded panel 702 and the threaded panel 704 extend above the first and second outer blades 105, 107. The first and second outer blades 105, 107 terminate in atop ledge 701 proximate the collar 308. The top ledge 701 is sized to allow the bottom surface 703 of connector 113 to abut the top ledge. The bottom surface 703 facilitates retention of the engagement pin 310 in the engagement bore 320.

Figure 8:
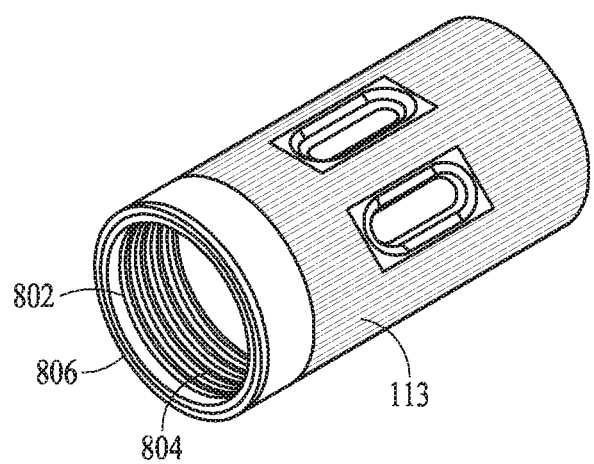
FIG. 8 is a perspective view of the connector of FIG. 1.

The collar 308 has a flared extension 705 that forms a cavity 707 between the flared extension 705 and the top non-threaded and threaded panels 702, 704. The connector, as shown in FIG. 8, is generally a hollow cylindrical tube with a lower threaded portion 802 that has threads 804 sized to cooperatively engage threads 706. The threads 706, 804 may be designed as reverse or "left-handed" such that the connector 113 is not inadvertently disengaged during conventional use. The cylindrical tube of connector 113 is formed by a wall having a thickness 806 sized to cooperatively fit in cavity 707. Threading the connector 113 onto the threaded panels 704 of the first and second inner blades 109, 111 coupled the first outer blade 105 and first inner blade 109 to the second outer blade 107 and the second inner blade 111.

Once the tool 100 is coupled and locked to saddle 102, the connector 113 may be removed. The first and second inner and outer blades 105, 107, 109, 111 generally retain their respective positions in the locked position 202 on the implant without the connector 113. Removal of the connector 113, as generally shown in FIG. 7, results in a channel 710 that extends the entire length of the first and second inner and outer blades 105, 107, 109, 111. Thus, unlike the aforementioned prior art tools, the rod may be inserted using a tool extending anywhere along the length of the channel 710. In other words, when the connector 113 is removed, the proximal opening of channel 710 is unblocked from access by a horizontal tool or rod and when the connector 113 is connected, the proximal opening to channel 710 is blocked by the connector 113 such that the channel cannot be accessed therefrom by a horizontal tool or rod. The hollow connector 113 allows the tool 100 to be used with other conventional tools as well.

Figure 9:
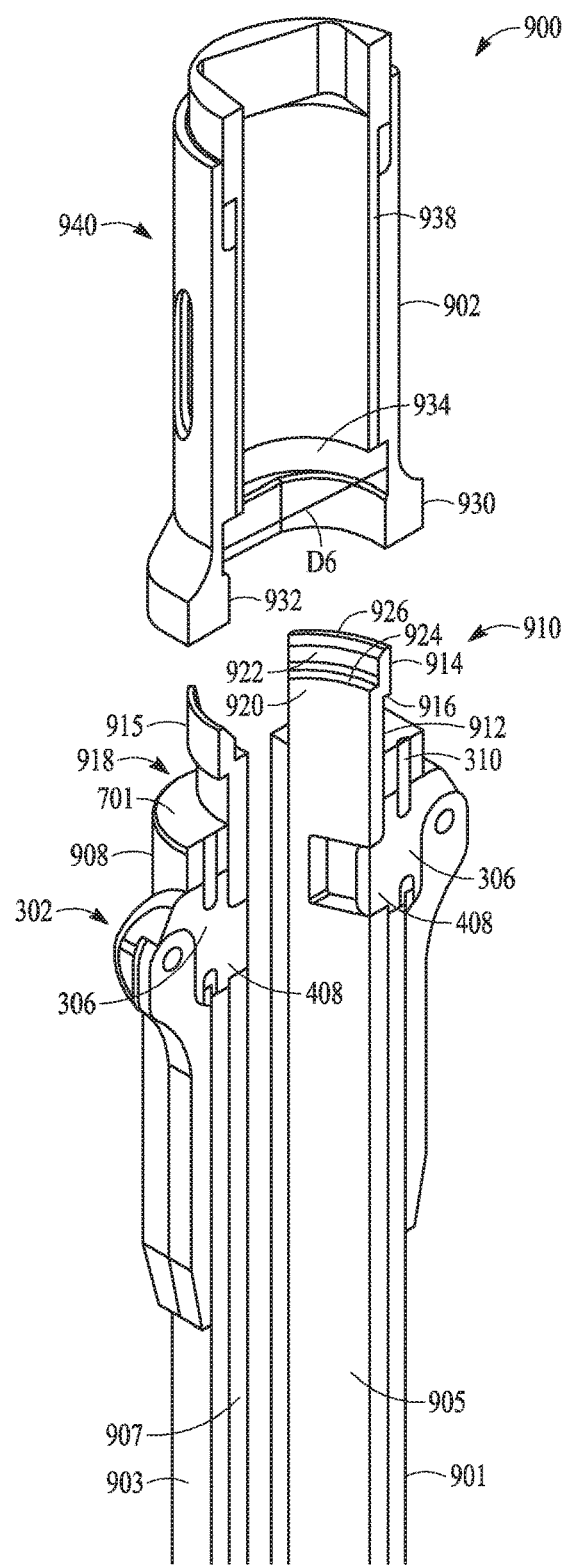
FIG. 9 is a partially exploded, perspective cross-sectional view of another tool consistent with the technology of the present application.
Figure 10:
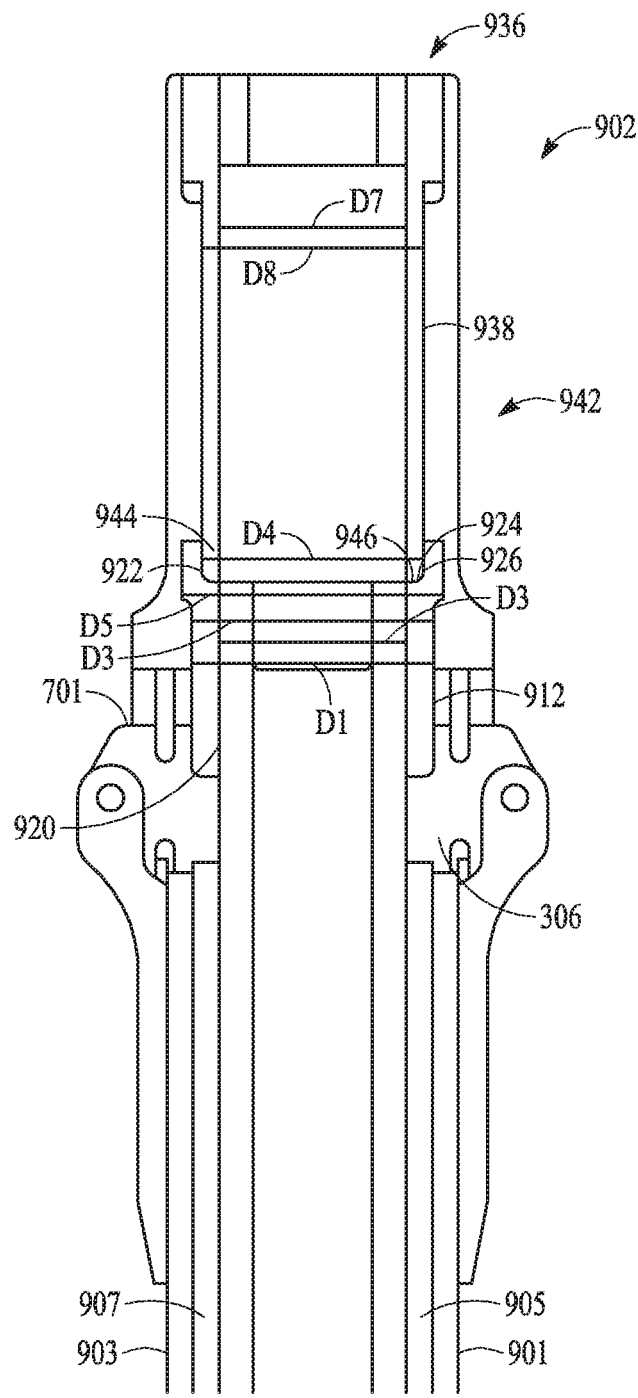
FIG. 10 is a cross-sectional view of the tool shown in FIG. 9.

With reference now to FIGS. 9 and 10, a tool 900 with an alternative connector 902 is provided. The tool 900 has first and second outer blades 901, 903 and first and second inner blades 905, 907. The inner and outer blades 901, 903, 905, 907 move in sliding relation to each other similar to the tool 100 described above. The tool 900 similarly has the turret 306 rotationally coupled to the blades 901, 903, 905, 907 such that rotation of the protrusion 408 moves the first and second inner blades 905, 907 between the locked and unlocked positions.

The first and second outer blades 901, 903 terminate in a collar 908 that contains the alignment bore 302. The collar 908 of tool 900 terminates in the top ledge 701. The top ledge 701 comprises the engagement bore 320 through which the engagement pin 310 extends to reside in the gap 416.

The first and second inner blades 905, 907 have a connector lock portion 910 extending beyond the top ledge 701. The connector lock portion 910 includes a first outer surface 912 having a first outer diameter D1 and a second outer surface 914 having a second outer diameter D2. The diameter D2 is greater than the diameter D1 such that the second outer surface 914 is stepped radially outward from the first outer surface 912 forming an overhang 916. The overhang 916, first outer surface 912, and top ledge 701 form a groove 918, channel or the like. The connector lock portion 910 includes a first inner surface 920 having a first inner diameter D3 and a second inner surface 922 having a diameter D4. The diameter D4 is greater than the diameter D3 such that the second outer surface 922 is stepped radially outward from the first inner surface 920 forming a ridge 924. The connector lock portion 910 terminates at a crown 926. The crown 926 may be flat or sloped. As shown, a portion of the crown 926 is sloped from the second outer surface 914 down towards the second inner surface 922. The slope, taper, or chamfer may facilitate the insertion of a lock wall as will be explained further below. The connector portion 910 has a lock tab 915 formed generally by the second outer surface 914, the crown 926, and the second inner wall 922.

The connector 902 has a base 930 with an inner rail 932. The inner rail 932 has a rail diameter D5 that is approximately equal to diameter D1 such that the inner rail 932 resides in groove 918. Adjacent the rail 932 is a ring 934. The ring 934 has a ring diameter D6 that is approximately equal to the diameter D2 such that the lock tab 915 resides in the ring 934.

The connector 902 comprises a hollow interior 936 to receive a movable barrel 938. The connector 902 connects first and second inner and outer blades 901, 903, 905, 907 by movement of the barrel 938 from an unlocked position 940 (shown in FIG. 9) where the first and second inner blades 905, 907 at the connector portion 910 may move radially inwardly to be snap fit with the connector 902 and a locked position 942 (shown in FIG. 10) where the barrel forms a lock wall 944 to retain the lock tab 915 in the ring 934 such that the first and second inner blades 905, 907 cannot move sufficiently radially inwardly to disengage from the connector 902. The barrel 938 has a bottom stop 946 that is supported by the ridge 924. The barrel 938 also is generally hollow to allow tool access. The barrel 938 proximate the bottom stop 946 has an inner diameter D7 approximately equal to diameter D3 and an outer diameter D8 approximately equal to diameter D4.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A tool, comprising:
   first and second outer blades each having a distal end and a proximal end, wherein the first and second outer blades each comprise an attachment mechanism disposed at the distal end for coupling the first and second outer blades to an implant, wherein the first and second outer blades each comprise an alignment bore in the proximal end;
   first and second inner blades each having a distal end and a proximal end, wherein the first and second inner blades each comprise an alignment window in the proximal end, wherein the alignment window of each of the first and second inner blades overlaps with the alignment bore of the corresponding one of the first and second outer blades, and wherein the first inner and outer blades and the second inner and outer blades cooperate to form a channel extending along an entire length of the first and second inner and outer blades; and
   first and second turrets, wherein each turret has a lever pivotally coupled thereto, wherein each turret is rotatably positioned in the alignment bore of the corresponding one of the first and second outer blades, wherein each turret comprises a protrusion that is movably positioned in the alignment window of the corresponding one of the first and second inner blades such that rotation of the turret causes movement of the protrusion, and wherein actuation of the lever rotates the turret and causes the first and second inner blades to move relative to the first and second outer blades about and between an unlocked position and a locked position.

2. The tool of claim 1, further comprising a hollow connector releasably coupled to the proximal end of the first and second inner blades, wherein a proximal end of the channel is blocked when the hollow connector is coupled to the first and second inner blades and wherein the proximal end of the channel is unblocked when the hollow connector is removed from the first and second inner blades.

3. The tool of claim 1, wherein the turret comprises an inside portion and an outside portion connected by a beam, and wherein the inside portion, the outside portion, and the beam cooperate to form an annular gap.

4. The tool of claim 3, wherein the first and second outer blades each further comprise a collar having an engagement bore; and further comprising an engagement pin positioned in the engagement bore and at least a portion of the annular gap, wherein the engagement pin retains and allows rotational movement of the turret in the engagement bore.

5. The tool of claim 3, wherein the outside portion of the turret has a lever channel defined therein and a hinge bore extending through the outside portion across the lever channel, wherein the lever comprises an arm having a rod bore defined therein, and wherein a rod extends through the hinge bore and the rod bore to pivotally couple the lever to the turret.

6. The tool of claim 1, wherein:
   each of the first and second outer blades each comprise a collar at the proximal end;
   each of the first and second inner blades comprise a connector lock portion extending beyond the collar, wherein the connector lock portion terminates in a lock tab; and
   the hollow connector comprises a base that abuts the collar, a ring sized to cooperatively engage the lock tab, and a barrel movable in the connector to form a lock wall preventing the lock tab from disengaging from the ring.

7. The tool of claim 6, wherein
   the collar terminates at a top ledge and the connector lock portion comprises a first outer surface, a second outer surface stepped radially outward from the first outer surface, and an overhang extending between the first outer surface and the second outer surface such that the top ledge, first outer surface, and overhang cooperate to form a groove; and
   the base comprises a rail sized to fit in the groove.

8. The tool of claim 6, wherein the lock tab and the barrel form a taper lock.

9. The tool of claim 1, wherein:
   each of the first and second outer blades each comprise a collar at the proximal end, the collar comprising a flared extension;

each of the first and second inner blades comprise an externally threaded portion extending beyond the collar and forming a gap between the flared extension and at least the externally threaded portion; and the connector comprises an internally threaded portion wherein the internally threaded portion cooperatively engages the externally threaded portion of the first and second inner blades.

10. The tool of claim 1, wherein the first and second inner blades are releasably coupleable to an implant at a first location.

11. The tool of claim 10, wherein the first and second outer blades are releasably coupleable to the implant at a second location different than the first location.

12. The tool of claim 10, wherein the first and second inner blades each comprise a protrusion engageable with a detent in the implant.

13. The tool of claim 11, wherein the first and second outer blades each comprise a ledge engageable with a shelf in the implant.

14. The tool of claim 13, wherein the implant is a saddle.

15. A system, comprising:
a tool having a proximal end and a distal end, the tool comprising a first portion and a second portion spaced from each other to form a channel extending a length thereof, each of the first and second portions comprising:

first and second arcuate elongate members, a turret, and an attachment mechanism disposed at a distal end of the first arcuate elongate member, wherein the first arcuate elongate member has an alignment bore disposed in a proximal end thereof and the second arcuate elongate member has an alignment window disposed in a proximal end thereof, wherein the first and second arcuate elongate members are positioned such that the alignment window overlaps with the alignment bore, wherein the turret comprises a protrusion and has a lever pivotably coupled thereto, wherein the turret is rotatably positioned in the alignment bore and the protrusion of the turret is movably positioned in the alignment window such that rotation of the turret moves the protrusion, and wherein actuation of the lever rotates the turret and causes the first elongate arcuate member to move relative to the second elongate arcuate member about and between a locked position and an unlocked position; and an implant comprising corresponding first and second attachment mechanisms to releasably attach to the corresponding attachment mechanism of the first portion and the second portion, respectively.

16. The system of claim 15, further comprising a connector releasably connecting the first and second portions at the proximal end of the tool, the connector comprising a hollow interior, wherein a proximal end of the channel is blocked when the connector is coupled to the first and second portions and wherein the proximal end of the channel is unblocked when the connector is removed from the first and second portions.

17. The system of claim 16, wherein the first and second portions of the tool are connected only by the connector and the implant.

18. The system of claim 16, wherein the connector comprises a base having a rail, a ring extending circumferentially around an inner wall, and a lock barrel movable along the inner wall; wherein the first arcuate elongated members terminate in a collar having a top ledge; wherein the second arcuate elongate members terminate in a connector portion sized to fit within the hollow interior of the connector; wherein the connector further comprises a lock tab sized to move in and out of the ring; and wherein the lock barrel has a connected position where the lock barrel engages the lock tab in the ring.

19. The system of claim 15, wherein the implant is a saddle.

* * * * *